(12) United States Patent
Maffei

(10) Patent No.: US 9,474,858 B2
(45) Date of Patent: Oct. 25, 2016

(54) DOSING METHOD WITH A DEVICE FOR TRANSFERRING AND DOSING BIOMEDICAL FLUIDS BETWEEN HOSPITAL CONTAINERS

(71) Applicant: Giuseppe Maffei, Mirandola (IT)

(72) Inventor: Giuseppe Maffei, Mirandola (IT)

(73) Assignee: PIERC DI GIOVANELLI GABRIELE E C. S.A.S., Cavezzo (MO) (IT)

( * ) Notice: Subject to any disclaimer, the term of this patent is extended or adjusted under 35 U.S.C. 154(b) by 0 days.

(21) Appl. No.: 14/987,927

(22) Filed: Jan. 5, 2016

(65) Prior Publication Data

US 2016/0129184 A1 May 12, 2016

Related U.S. Application Data

(63) Continuation of application No. 13/877,265, filed as application No. PCT/IB2011/002622 on Nov. 7, 2011, now abandoned.

(30) Foreign Application Priority Data

Nov. 9, 2010 (IT) .............................. MO2010A0319

(51) Int. Cl.
*A61M 5/20* (2006.01)
*A61M 5/145* (2006.01)
(Continued)

(52) U.S. Cl.
CPC . *A61M 5/20* (2013.01); *A61J 1/18* (2013.01); *A61J 1/2096* (2013.01); *A61J 1/22* (2013.01);
(Continued)

(58) Field of Classification Search
CPC ............. A61M 5/20; A61M 5/14566; A61M 5/14546; A61M 5/1782; A61M 5/1452; A61M 2205/14; A61M 2205/8206; B65B 3/003

USPC ........ 141/18, 25–27, 98, 389, 383; 222/386, 222/390, 333; 604/218, 224, 232, 233
See application file for complete search history.

(56) References Cited

U.S. PATENT DOCUMENTS 5,269,762 A 12/1993 Armbruster et al.
5,672,155 A * 9/1997 Riley ...................... A61M 5/20
604/131

(Continued)

FOREIGN PATENT DOCUMENTS

EP 0577354 1/1994
EP 1236644 9/2002

OTHER PUBLICATIONS

International Search Report, dated Feb. 29, 2012, from corresponding PCT application.

*Primary Examiner* — Mark A Laurenzi
*Assistant Examiner* — Timothy P Kelly
(74) *Attorney, Agent, or Firm* — Young & Thompson

(57) ABSTRACT

A dosing method using a device for transferring and dosing biomedical fluids between hospital containers includes a syringe body containing a biomedical fluid and a piston sealed fitted therein, the syringe body including a first extremity having joining elements to a first container and to a second container, and a second extremity opposite the first extremity, the method including gripping a handle having a coupling seat for fastening to the second extremity; placing first temporary fastening elements between the coupling seat and second extremity; placing second temporary fastening elements between the piston and thrust rod; operating a thrust rod of a motorized element mounted in the handle for pushing the piston; and dosing using control elements mounted on the handle, associated with the motorized element to dose volumetric quantities of biomedical fluid from the first container and dispensing to the second container.

14 Claims, 3 Drawing Sheets

(51) Int. Cl.
- *A61J 1/18* (2006.01)
- *A61J 1/20* (2006.01)
- *A61J 1/22* (2006.01)
- *A61M 5/172* (2006.01)

(52) U.S. Cl.
CPC ......... *A61M 5/14566* (2013.01); *A61M 5/172* (2013.01); *A61M 2205/502* (2013.01); *A61M 2205/52* (2013.01)

(56) References Cited

U.S. PATENT DOCUMENTS

| | | |
|---|---|---|
| 5,911,252 A | 6/1999 | Cassel |
| 6,056,165 A | 5/2000 | Speranza |
| 6,929,619 B2 | 8/2005 | Fago et al. |
| 7,887,513 B2 | 2/2011 | Nemoto et al. |

* cited by examiner

DOSING METHOD WITH A DEVICE FOR TRANSFERRING AND DOSING BIOMEDICAL FLUIDS BETWEEN HOSPITAL CONTAINERS

TECHNICAL FIELD

The present invention relates to a dosing method using a device for transferring and dosing biomedical fluids between hospital containers.

BACKGROUND ART

With particular reference to the oncology sector, but not only, it is known that to carry out numerous types of therapeutic treatments, the patients are connected to a parenteral infusion line placed in communication with a series of bags containing the drugs to be administered.

Each bag is connected to the infusion line independently from the others by means of a series of valves and the dispensing of the drugs to the patient is done in succession, placing between the administration of one drug and the next an intermediate stage of cleaning of the infusion line by means of a lavage of a saline solution, so as to avoid any type of contamination between drugs.

In other words, these types of therapeutic treatments consist in the following sequence of operations: administering of the first drug, cleaning of the infusion line, administering of the second drug, new cleaning of the infusion line, administering of the third drug, and so on.

The drugs continue to be administered until the relevant bags containing the necessary doses prescribed by the doctor for the correct therapeutic treatment are completely empty.

The filling of the bags with the above doses occurs during a delicate preliminary stage during which a hospital operator, with care and attention, doses the necessary quantities inside the bags.

To perform this operation, the hospital technician usually has at disposal a series of bottles containing the drugs, from which he/she takes the required quantities and transfers these into the bags by means of a plurality of syringes (one for each drug, to avoid, in this case as well, any possible contamination between the fluids).

For this purpose, each syringe is made up of a syringe body made of transparent material, on which is shown a graduated measuring scale and inside which is fitted, sealed, a sliding piston, which is manually operated by the operator by means of a thrust rod.

The entire operation of taking, dosing and transferring drugs from the bottles to the bags, therefore, is performed in a completely manual way and without any automation, suctioning each drug inside the syringe body until the preset quantity is achieved indicated on the graduated scale and, then, dispensing the contents of the syringe inside the corresponding bag.

As will be easily appreciated by a person expert in the sector, this sequence of operations involves a series of drawbacks, including the fact that, for the correct transfer and dosing of the drugs, the strength, capacity and experience of the operator are all important in performing such operation.

In this respect, it must be pointed out that the considerable frequency with which these operations are performed often causes pain and/or lesions to the hands of the operator, who has to manually force on the thrust rod to draw the drugs up inside the syringes and, subsequently, to dispense them.

At the same time, the fact cannot be ignored that the correct dosing of the drugs inside the syringes depends only on the care and skill of the operator and that, in the case of wrong dosage, the risk exists of compromising the successful outcome of the therapy prescribed by the doctor during the patient administering stage.

In this respect, it must be underscored that the repetitiveness and monotony of the dosing operation cannot but increase the risk of lack of attention on the part of the operator while performing his/her duties and, consequently, the probability of an imprecise and incorrect dosage.

DESCRIPTION OF THE INVENTION

The main aim of this invention is to provide a dosing method using a device for transferring and dosing biomedical fluids between hospital containers which is portable and versatile, allows dosing biomedical fluids in a practical, easy, functional and precise way, allows reducing the efforts on the part of the operator and the consequent accidents/lesions, and allows reducing the risk of human error without changing the normal use procedure and/or the work schedules.

Another object of this invention is to provide a dosing method using a device for transferring and dosing biomedical fluids between hospital containers that allows overcoming the mentioned drawbacks of the state of the art in the ambit of a simple, rational, easy and effective to use as well as low cost solution.

The above objects are achieved by the present method, using the device for transferring and dosing biomedical fluids between hospital containers, comprising at least a syringe body for the containment of a biomedical fluid and at least a piston sealed fitted in a sliding way in said syringe body, said syringe body comprising a first extremity, having joining means to at least a first container from which taking the biomedical fluid and to at least a second container in which dispensing said biomedical fluid, and a second extremity opposite said first extremity, characterised by the fact that it comprises:
  a user manually gripping a handle having a coupling seat for the fastening to said second extremity of the syringe body;
  operating a motorised means mounted in said handle for the operation of a thrust rod suitable for pushing said piston;
  placing a first temporary fastening means between said coupling seat and said second extremity of the syringe body;
  placing a second temporary fastening means between said piston and said thrust rod; and
  dosing using control means mounted on said handle, associated with said motorised means and suitable for the volumetric dosing both of the quantity of said biomedical fluid to take from said first container and of the quantity of said biomedical fluid to dispense in said second container.

BRIEF DESCRIPTION OF THE DRAWINGS

Other characteristics and advantages of the present invention will become more evident from the description of a preferred, but not sole, embodiment of a method and device for transferring and dosing biomedical fluids between hospital containers, illustrated purely as an example but not limited to the annexed drawings in which.

EMBODIMENTS OF THE INVENTION

With particular reference to such figures, a device for transferring and dosing biomedical fluids between hospital containers is globally indicated by 1.

In this respect, it must be underscored that in this treatise the term "biomedical fluid" means any liquid used in the medical/hospital field and intended to be administered to a patient by means of bags or other containers and which requires being precisely pre-dosed.

Figure 1:
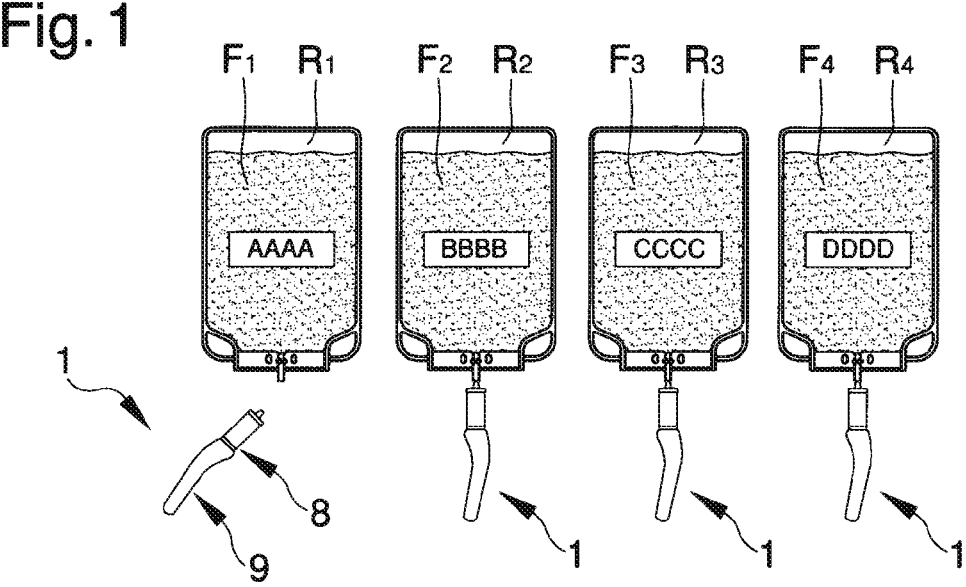
FIG. 1 is a front, schematic and partial view that illustrates an infusion line using the devices according to the invention to transfer and dose biomedical fluids.
Figure 1:
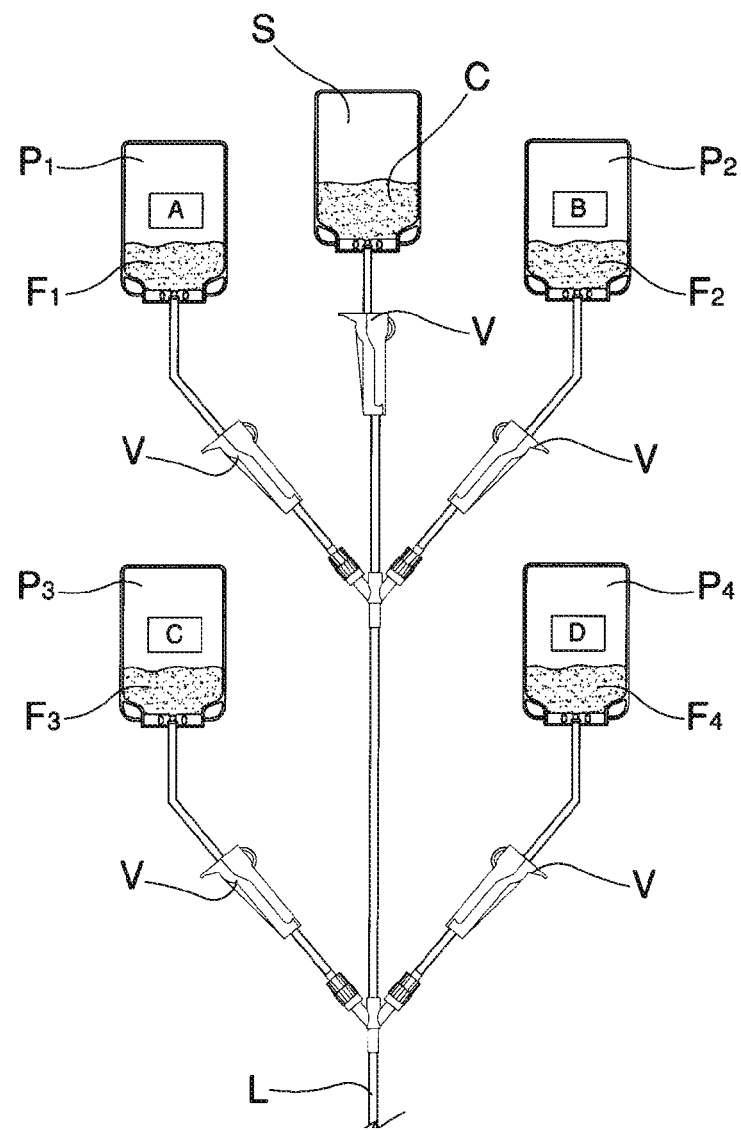
Figure 2:
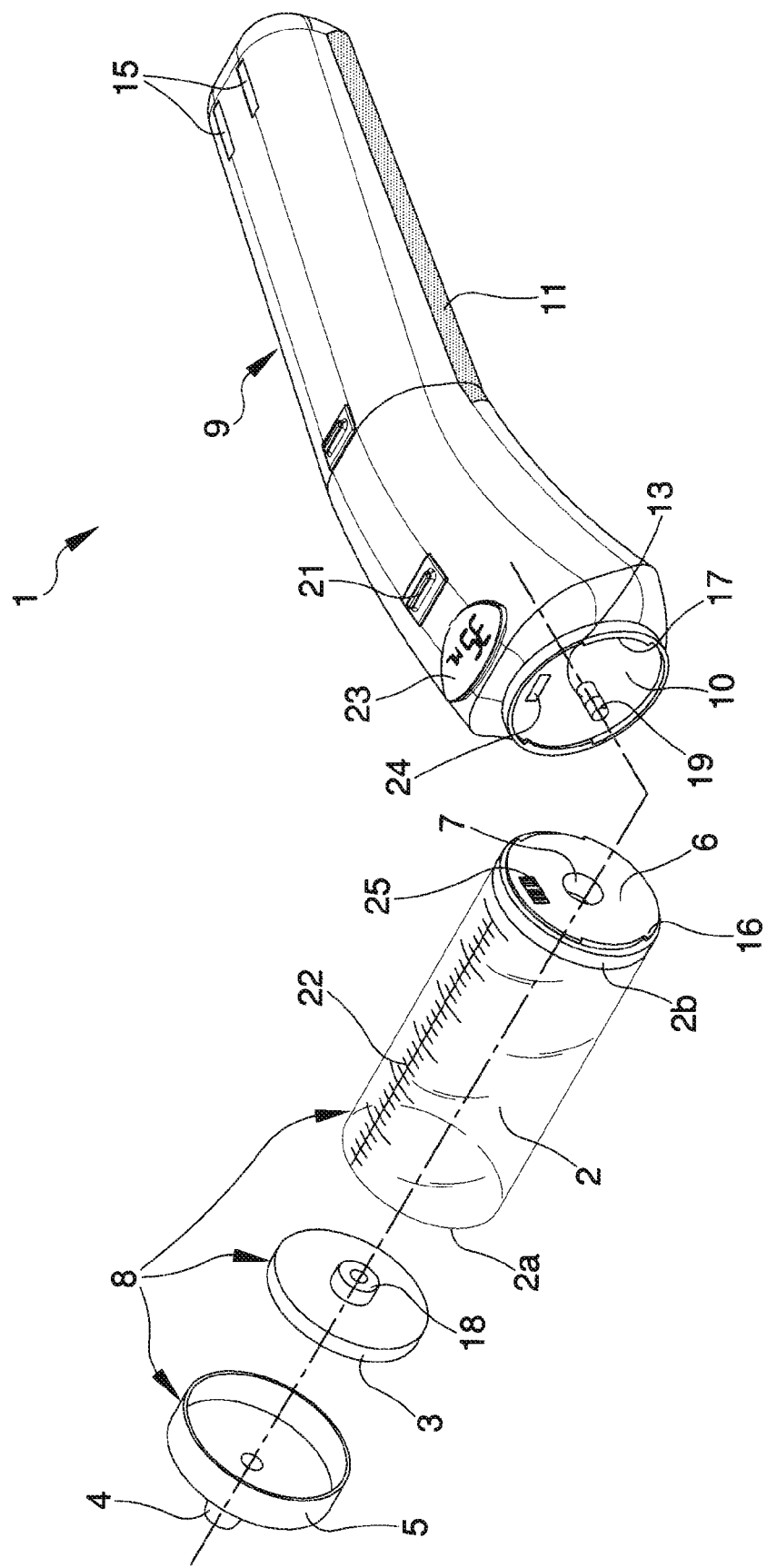
FIG. 2 is an exploded, schematic and partial view of a device according to the invention.
Figure 3:
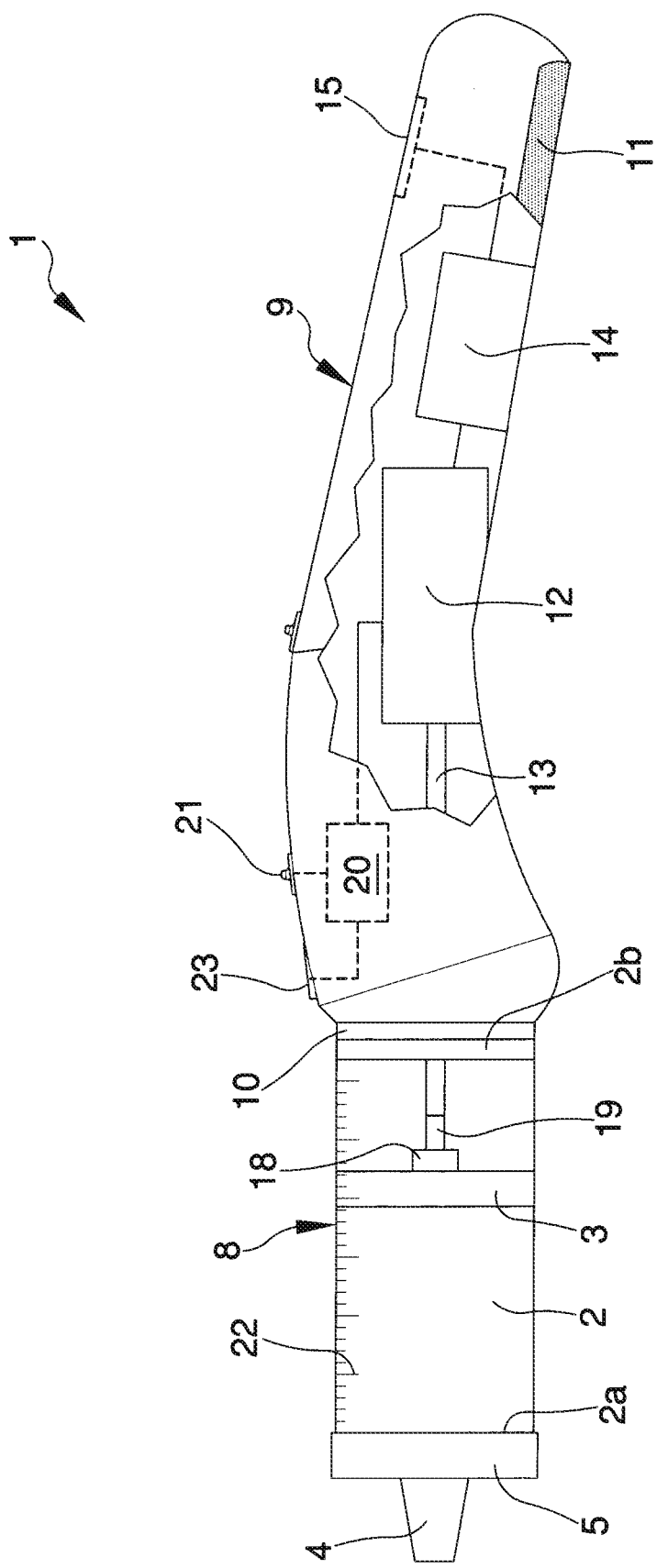
FIG. 3 is a side view of the device of FIG. 2.

In the particular embodiment shown in FIG. 1, the biomedical fluids consist of a series of drugs $F_1$, $F_2$, $F_3$, $F_4$, e.g., for oncology therapy use, contained in an equal number of first containers $R_1$, $R_2$, $R_3$, $R_4$ such as bottles or the like.

In the method, the biomedical fluids $F_1$, $F_2$, $F_3$, $F_4$ must be taken from the bottles $R_1$, $R_2$, $R_3$, $R_4$ and dispensed into an equal number of second containers $P_1$, $P_2$, $P_3$, $P_4$, of the type of bags or the like, to be connected to an infusion line L having a bag S of saline solution C and having specific cutout valve means V.

To transfer and dose the biomedical fluids $F_1$, $F_2$, $F_3$, $F_4$ the method uses a plurality of devices 1, one for each drug $F_1$, $F_2$, $F_3$, $F_4$.

Each device 1 comprises a syringe body 2 for containing the biomedical fluid $F_1$, $F_2$, $F_3$, $F_4$ and a piston 3 seal fitted sliding in the syringe body 2.

The syringe body 2 is composed of, e.g., a cylinder-shaped tubular element made of transparent, coloured or matt plastic material (polyurethane, polycarbonate, polyethylene, etc.).

The dimensions of the syringe body 2 can usefully vary according to the required containing capacity (e.g.: 10 ml, 20 ml, 30 ml, 50 ml, 60 ml).

The syringe body 2 has a first extremity 2a, having joining means 4 for joining to the first containers $R_1$, $R_2$, $R_3$, $R_4$ and to the second containers $P_1$, $P_2$, $P_3$, $P_4$, and a second extremity 2b opposite the first extremity 2a.

More in detail, the first extremity 2a terminates with an extremity cap 5 supporting the joining means 4, which, preferably, are of the Luer and Luer-Lock type.

The second extremity 2b, on the other hand, is shaped to define a cross separation wall 6, having a central hole 7.

The whole, made up of a syringe body 2, piston 3 and extremity cap 5 in point of fact makes up an interchangeable cartridge 8, which can be distributed on the market already assembled, i.e., with the piston 3 already fitted in the syringe body 2 through the first extremity 2a and with the first extremity 2a closed again by means of the extremity cap 5.

Each device 1 also comprises a handle 9 for the manual grip by a user and has a coupling seat 10 for fastening to the second extremity 2b of the syringe body 2.

The handle 9 has an ergonomic shape, with at least a portion in anti-slip material 11 to increase the fastness and the grip of the user's hand.

Inside the handle 9 are fitted motorised means 12 to drive a thrust rod 13 suitable for pushing the piston 3.

The motorised means 12, e.g., are made up of a linear actuator connected to the thrust rod 13 and suitable for achieving the straight to-and-from movement of the thrust rod 13.

The motorised means 12 are associated with a power supply battery 14 mounted in the handle 9; the power supply battery 14 is preferably of the rechargeable type and is associated with two terminals 15 for connecting to a recharging station, but alternatively, it cannot be ruled out that this is made up of one or more disposable type batteries.

The cartridge 8 is intended to be fitted on the handle 9 with the cross separation wall 6 facing the coupling seat 10, in correspondence to which the thrust rod 13 protrudes from the handle 9 and is intended to cross the transit hole 7 to operate the piston 3.

Between the coupling seat 10 and the second extremity 2b of the syringe body 2 are placed first temporary fastening means 16, 17, for the slot-in fitting of the cartridge 8 on the handle 9.

Similarly, between the piston 3 and the thrust rod 13 are placed second temporary fastening means 18, 19 to allow the connection and dragging of the piston 3 by the thrust rod 13.

The first temporary fastening means 16, 17 and the second temporary fastening means 18, 19, e.g., are of the bayonet type, but it cannot be ruled out that alternatively they be slotted in or consist of a connection by friction or the like. On the handle 9, furthermore, are fitted control means 20, 21 associated with the motorised means 12 and suitable for controlling their operation to obtain the volumetric dosage, including the micro-volumetric type dosage, both of the quantity of biomedical fluid $F_1$, $F_2$, $F_3$, $F_4$ to be taken from the first containers $R_1$, $R_2$, $R_3$, $R_4$, and of the quantity of biomedical fluid $F_1$, $F_2$, $F_3$, $F_4$ to be dispensed into the second containers $P_1$, $P_2$, $P_3$, $P_4$.

The control means 20, 21 comprise a processing and control unit 20 and a control interface 21, of the type of a keypad or the like, for controlling the motorised means 12 and designed to start/stop/set the processing and control unit 20 according to the user's requirements.

For this purpose, the processing and control unit 20 can usefully be of the programmable type to set the quantities of biomedical fluid $F_1$, $F_2$, $F_3$, $F_4$ to be taken and/or dispensed.

In this case, once set, the processing and control unit 20 is able to operate the thrust rod 13 independently for a section of stroke corresponding to the quantity of biomedical fluid $F_1$, $F_2$, $F_3$, $F_4$ to be taken and/or to be dispensed.

Alternatively, the syringe body 2 can show a graduated scale 22, the stop of the piston 3 during the taking/dispensing stage of the biomedical fluid $F_1$, $F_2$, $F_3$, $F_4$ being entrusted to the care and skill of the user.

The handle 9 also has display means 23, of the type of an electronic display or the like, suitable for showing the operating parameters of the processing and control unit 20 and, more in general, all types of information useful for the user.

On the handle 9 are also provided identification means 24 for identifying at least one between the syringe body 2 and the piston 3.

The identification means 24 are electronically associated with the processing and control unit 20 and suitable for preventing the operation of the motorised means 12 in case of the syringe body 2 and/or the piston 3 not being identified. This particular solution allows ensuring that the handle 9 is used correctly only with cartridges 8 of certified origin so as:
  to prevent the handle 9 being used with cartridges 8 made by third manufacturers;
  to guarantee to customers a high quality and functionality of the cartridges 8;
  to protect the market share of the legitimate manufacturer/vendor.

The identification means 24 are of the type of a reader chosen from the list comprising: bar code readers, optical readers, electromagnetic readers.

In the particular embodiment of the present invention shown in the illustrations, e.g., the identification means 24 are made up of a bar code reader designed to recognise a bar code 25 shown on the cross separation wall 6.

Alternative embodiments cannot however be ruled out wherein the identification means 24 are of different type and, e.g., consist of an RFID magnetic recognition system.

The handle 9 comprises means for recognising the correct coupling of the first temporary fastening means 16, 17 and of the second temporary fastening means 18, 19.

Such recognition means, not shown in detail in the illustrations, are associated with the processing and control unit 20 and suitable for preventing the operation of the motorised means 12 in case of incorrect coupling of the first temporary fastening means 16, 17 and of the second temporary fastening means 18, 19.

The recognition means made in this way allow the device 1 to operate in conditions of utmost safety only in the case of both the syringe body 2 and the piston 3 being stably coupled, with slot-in coupling, to the coupling seat 10 and to the thrust rod 13 respectively, so as to prevent their accidental disassembly during use.

The present invention operates as follows.

Each handle 9 is prepared to be conveniently used with an indefinite number of cartridges 8 inasmuch, at the end of their normal life cycle, these can be separated from the handle 9, rejected and replaced by new ones.

At the start of the life cycle of each cartridge 8, this is coupled on the handle 9 being careful to correctly couple the syringe body 2 to the coupling seat 10.

Once the first temporary fastening means 16, 17 have been coupled, the processing and control unit 20 automatically commands the forward movement of the thrust rod 13 until this is coupled with the piston 3.

In this phase, the processing and control unit 20 proceeds to identify the cartridge 8 by means of the identification means 24 and performs recognition of the correct coupling of the first temporary fastening means 16, 17 and of the second temporary fastening means 18, 19 and, in the case of positive outcome, allows the subsequent operation of the motorised means 12.

At this point all the user has to do is connect the joining means 4 to the corresponding first container $R_1$, $R_2$, $R_3$, $R_4$ and, by means of the control means 20, 21, perform the withdrawal of the required quantity of biomedical fluid $F_1$, $F_2$, $F_3$, $F_4$ and fill the syringe body 2.

Afterwards, by coupling the joining means 4 to the second corresponding container $P_1$, $P_2$, $P_3$, $P_4$, the biomedical fluid $F_1$, $F_2$, $F_3$, $F_4$ can be dispensed and the device 1 is ready for the subsequent operations.

Using the same handle 9 and the same cartridge 8, all the transfers can be made of the biomedical fluid $F_1$, $F_2$, $F_3$, $F_4$ contemplated according to the normal life cycle of the syringe body 2 and of the piston 3.

After various uses and after some time from the first use, in fact, the cartridge 8 becomes worn and contaminated and has to be replaced with a new one in the same way as previously described and shown.

As it has been said, in the embodiment shown in the FIG. 1, the use is contemplated of a plurality of devices 1, or at least a plurality of handles 9, one for each drug $F_1$, $F_2$, $F_3$, $F_4$, but nothing prevents having just one handle 9 and a plurality of cartridges 8 to be used alternately with the handle 9 to transfer the drugs $F_1$, $F_2$, $F_3$, $F_4$, being careful to use each cartridge 8 with one and only one drug $F_1$, $F_2$, $F_3$, $F_4$.

The invention claimed is:

1. A dosing method for transferring and dosing biomedical fluids between hospital containers for administration to a patient, said method comprising the steps of:
    obtaining a device with a syringe body (2) for containing a biomedical fluid ($F_1$, $F_2$, $F_3$, $F_4$) and a piston (3) sealed fitted in a sliding way in said syringe body (2), said syringe body (2) comprising a first extremity (2a) and a second extremity (2b) opposite said first extremity (2a);
    a user manually gripping a handle (9) having a coupling seat (10), and fastening the coupling seat (10) to said second extremity (2b) of the syringe body (2) so that the handle is attached to the device, the handle comprising a linear actuator (12) connected to a thrust rod (13), the linear actuator (12) in operation provides movement of the thrust rod (13), the linear actuator (12) being user-controlled by a control unit (20) and a control interface (21) programmable to set a quantity of the biomedical fluid ($F_1$, $F_2$, $F_3$, $F_4$) to be dispensed from or taken into the syringe body of the device,
    wherein fastening the coupling seat (10) to said second extremity (2b) of the device includes placing i) a first temporary fastening means (16, 17) placed between said coupling seat (10) and said second extremity (2b), and ii) placing a second temporary fastening means (18, 19) between said piston (3) and said thrust rod (13);
    joining the first extremity (2a) of said device to a first container ($R_1$, $R_2$, $R_3$, $R_4$) to accept the biomedical fluid ($F_1$, $F_2$, $F_3$, $F_4$) from the first container ($R_1$, $R_2$, $R_3$, $R_4$);
    the user performing a first programming the control interface (21) to set a first desired quantity of the biomedical fluid ($F_1$, $F_2$, $F_3$, $F_4$) to be taken into the syringe body of said first device from the first container ($R_1$, $R_2$, $R_3$, $R_4$);
    the user performing a first operating of the control interface to have the linear actuator (12) move the thrust rod (13) to provide a pushing motion on said piston (3) of said device that corresponds to first desired quantity of the biomedical fluid ($F_1$, $F_2$, $F_3$, $F_4$) to take into the syringe body the first desired quantity of the biomedical fluid ($F_1$, $F_2$, $F_3$, $F_4$) from the first container ($R_1$, $R_2$, $R_3$, $R_4$);
    the user performing a second programming the control interface to set a second desired quantity of the biomedical fluid ($F_1$, $F_2$, $F_3$, $F_4$) to be dispensed from the syringe body into a second container ($P_1$, $P_2$, $P_3$, $P_4$);
    the user joining the first extremity (2a) of said device to the second container ($P_1$, $P_2$, $P_3$, $P_4$) to dispense the second desired quantity of the biomedical fluid ($F_1$, $F_2$, $F_3$, $F_4$) into the second container ($P_1$, $P_2$, $P_3$, $P_4$); and
    the user performing a second operating of the control interface to have the linear actuator (12) move the thrust rod (13) to provide another pushing motion on said piston (3) of said device that corresponds to second desired quantity of the biomedical fluid ($F_1$, $F_2$, $F_3$, $F_4$) to dispense from the syringe body the second desired quantity of the biomedical fluid ($F_1$, $F_2$, $F_3$, $F_4$) into the second container ($P_1$, $P_2$, $P_3$, $P_4$), thereby dosing the second container ($P_1$, $P_2$, $P_3$, $P_4$) with the biomedical fluid ($F_1$, $F_2$, $F_3$, $F_4$) taken from the first container ($R_1$, $R_2$, $R_3$, $R_4$).

2. The dosing method according to the claim 1, wherein said joining the first extremity (2a) of said device to the first container ($R_1, R_2, R_3, R_4$) to accept the biomedical fluid ($F_1, F_2, F_3, F_4$) from the first container ($R_1, R_2, R_3, R_4$), includes removing an extremity cap (5) from the first extremity (2a).

3. The dosing method according to the claim 1, wherein in at least one of said user programming steps the user uses a display (23) mounted on said handle (9) that shows operating parameters of said control unit (20).

4. The dosing method according to the claim 1, wherein said step of fastening the coupling seat (10) to said second extremity (2b) of the syringe body (2), the user recognizes correct coupling of the first temporary fastening means (16, 17) between said coupling seat (10) and said second extremity (2b).

5. The dosing method according to the claim 1, wherein said step of fastening the coupling seat (10) to said second extremity (2b) of the syringe body (2), the user recognizes correct coupling of the second temporary fastening means (18, 19) between said piston (3) and said thrust rod (13).

6. The dosing method according to the claim 1, wherein said step of fastening the coupling seat (10) to said second extremity (2b) of the syringe body (2), the user uses a bayonet fastening means as the first temporary fastening means (16, 17) between said coupling seat (10) and said second extremity (2b).

7. The dosing method according to the claim 1, wherein said step of fastening the coupling seat (10) to said second extremity (2b) of the syringe body (2), the user uses a bayonet fastening means as the second temporary fastening means (18, 19) between said piston (3) and said thrust rod (13).

8. The dosing method according to the claim 1, wherein said step of fastening the coupling seat (10) to said second extremity (2b) of the syringe body (2), the user ensures said thrust rod (13) transits a hole (7) of a cross separation wall (6) at said second extremity (2b) of the corresponding syringe body (2).

9. The dosing method according to the claim 1, wherein said biomedical fluid (F1, F2, F3, F4) is an oncology fluid, said second container ($P_1, P_2, P_3, P_4$) is a bag containing drugs to be administered to the patient, said bag including a parenteral infusion line, said method further comprising using the parenteral infusion line to administer the drugs in said second container ($P_1, P_2, P_3, P_4$) to the patient.

10. The dosing method according to the claim 9, wherein each of a plurality of said second container ($P_1, P_2, P_3, P_4$) is dosed with desired quantities of different biomedical fluid ($F_1, F_2, F_3, F_4$) in accordance with said joining steps, said first and second programming steps, and said first and second operating steps being performed using a different one of said device for each said different biomedical fluid ($F_1, F_2, F_3, F_4$) such that a different said device (1) is used for each different biomedical fluid ($F_1, F_2, F_3, F_4$);

a downstream side of the parenteral infusion lines said second containers ($P_1, P_2, P_3, P_4$) are joined, via respective cutout valves (V), to a common infusion line (L); and using the common infusion line to sequential administer each of the drugs in each respective said second container (P1, P2, P3, P4) to the patient.

11. The dosing method according to the claim 1, wherein said second container (P1, P2, P3, P4) is a bag containing drugs to be administered to the patient, said bag including an infusion line, said method further comprising using the infusion line to administer the drugs in said second container (P1, P2, P3, P4) to the patient.

12. The dosing method according to the claim 11, wherein, each of a plurality of said second container (P1, P2, P3, P4) is dosed with desired quantities of different biomedical fluid ($F_1, F_2, F_3, F_4$) in accordance with said joining steps, said first and second programming steps, and said first and second operating steps being performed using a different one of said device for each said different biomedical fluid ($F_1, F_2, F_3, F_4$) such that a different said device (1) is used for each different biomedical fluid ($F_1, F_2, F_3, F_4$);

a downstream side of the parenteral infusion lines said second containers (P1, P2, P3, P4) are joined, via respective cutout valves (V), to a common infusion line (L); and using the common infusion line to sequential administer each of the drugs in each respective said second container (P1, P2, P3, P4) to the patient.

13. The dosing method according to the claim 1, wherein the first container (R1, R2, R3, R4) is a bottle and the second container (P1, P2, P3, P4) is a bag.

14. The dosing method according to the claim 10, wherein said first container (R1, R2, R3, R4) is a bottle and each said second container (P1, P2, P3, P4) is a bag.

* * * * *